US007008410B2

(12) United States Patent
Gustin et al.

(10) Patent No.: US 7,008,410 B2
(45) Date of Patent: Mar. 7, 2006

(54) ABSORBENT ARTICLE

(75) Inventors: Maria Gustin, Göteborg (SE); Katharina Karlsson, Härryda (SE)

(73) Assignee: SCA Hygiene Products AB, Gothenburg (SE)

( * ) Notice: Subject to any disclaimer, the term of this patent is extended or adjusted under 35 U.S.C. 154(b) by 31 days.

(21) Appl. No.: 09/950,668

(22) Filed: Sep. 13, 2001

(65) Prior Publication Data
US 2002/0058924 A1   May 16, 2002

Related U.S. Application Data

(60) Provisional application No. 60/232,136, filed on Sep. 13, 2000.

(30) Foreign Application Priority Data
Sep. 13, 2000   (SE) ................................. 0003253

(51) Int. Cl.
A61F 13/15   (2006.01)

(52) U.S. Cl. ...................................... 604/392; 604/394

(58) Field of Classification Search ........... 604/385.01, 604/385.03, 386, 387, 389, 392–394, 368
See application file for complete search history.

(56) References Cited

U.S. PATENT DOCUMENTS 3,618,608 A * 11/1971 Brink .......................... 604/391
3,929,134 A * 12/1975 Karami ........................ 604/378
5,135,522 A *  8/1992 Fahrenkrug et al. ...... 604/385.3
5,374,262 A * 12/1994 Keuhn et al. ................ 604/391
5,549,593 A *  8/1996 Ygge et al. .................. 604/391
5,685,873 A * 11/1997 Bruemmer ............... 604/385.2
5,971,970 A * 10/1999 Carlbark et al. ........ 604/385.03
6,241,716 B1 *  6/2001 Ronnberg .................... 604/391
6,306,121 B1 * 10/2001 Damaghi et al. ....... 604/385.03

FOREIGN PATENT DOCUMENTS

WO       97/38658      10/1997
WO       99/21522       5/1999

* cited by examiner

Primary Examiner—Tatyana Zalukaeva
Assistant Examiner—C. Lynne Anderson
(74) Attorney, Agent, or Firm—Buchanan Ingersoll P.C.

(57) ABSTRACT

Absorbent article such as a diaper and an incontinence guard comprising a pair of belt portions (9) attached to the rear portion (6) alternatively the front portion (5) of the article and which are intended to be fastened together around the waist of the wearer and where said front portion (5) alternatively the rear portion (6) is provided with fastening means (8), intended to be attached to the belt portions (9), in such a way that the article will assume a pantlike shape, where the belt portions (9) form a part of the waist portions of the pant. Said belt portions (9) are provided with stiffening elements (11), being discontinuously arranged in the longitudinal direction (x) of the belt, and whose largest extension substantially being arranged across the longitudinal direction (x) of the belt.

6 Claims, 2 Drawing Sheets

ABSORBENT ARTICLE

This application claims the benefit of Provisional application Ser. No. 60/232,136, filed Sep. 13, 2000.

TECHNICAL FIELD

The present invention refers to an absorbent article such as a diaper and an incontinence guard comprising a liquid permeable topsheet, a liquid impermeable backsheet and an absorbent body enclosed therebetween, said article having a front portion, a rear portion and a crotch portion therebetween, and further is provided with a pair of belt portions attached to the rear portion of the article and which are intended to be fastened together around the waist of the wearer and where said front portion is provided with attachment means intended to be attached to the belt portions, in such a way that the article will assume a pantlike shape, where the belt portions form a part of the waist portions of the pant.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is further known, through, e.g., EP-A-0 287 388, EP-A-0 409 307, EP-A-0 528 282, EP-A-0 605 012 and FR-A-2 586 558, to attach the front and rear portions of the article by means of a belt, at which the possibilities to adjust the fit are improved. The belt further provides a simplified change of diaper or incontinence guard, especially when the patient is standing up.

On a common type of belt diaper the belt portions are first attached around the waist of the patient and then the front portion of the diaper is attached to the outside of the belt using hook and loop fasteners or tape tabs, being arranged on the belt and/or the front portion. One problem is that the belt folds itself longitudinally upon usage, which leads to discomfort for the wearer.

WO 99/21522 describes a belt whose cross-section varies in stiffness. This leads to an increased comfort for the wearer. The belt adapts itself to some extent after the wearer since it is more flexible at the edges. However, the elements are longitudinally arranged in the belt which might lead to sagging of the belt anyhow.

It would therefore be desirable to provide a diaper or incontinence guard having a comfortable belt which fits persons having different sizes.

SUMMARY OF THE INVENTION

The object of the present invention is to accomplish a belt to a diaper or incontinence guard being comfortable to wear and which will fit differently sized persons. This object has been solved in that the belt portions are provided with stiffening elements, being discontinuously arranged in the longitudinal direction of the belt, and whose largest extension is arranged essentially across the belt in relation to the longitudinal direction of the belt. These element makes the belt fully outstretched without sagging and distributes the force equally over the belt, which gives an increased comfort.

BRIEF DESCRIPTION OF DRAWINGS

The invention will in the following be closer described with reference to an embodiment shown in the accompanying drawings.

DESCRIPTION OF AN EMBODIMENT

Figure 1:
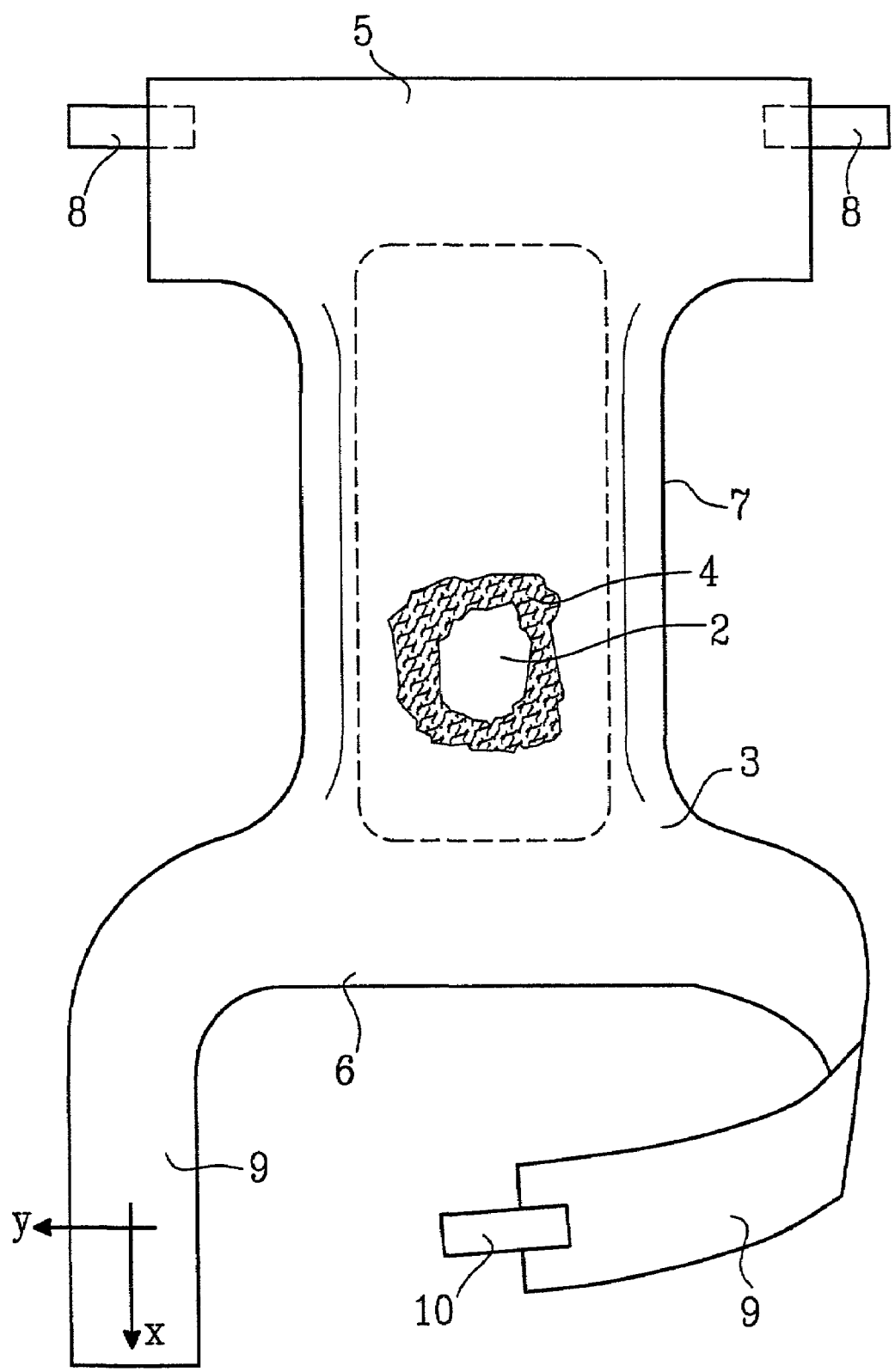
FIG. 1 shows schematically a perspective view of a diaper or incontinence guard according to the invention.

The drawing shows an embodiment of a diaper or incontinence guard 1 comprising a liquid impermeable backsheet 2, a liquid permeable topsheet 3 and an absorbent body 4 enclosed therebetween. The liquid permeable topsheet 3 can include a nonwoven material, e.g., a spunbond material of continuous filaments, a meltblown material, a bonded carded fibrous web or a perforated plastic film. The liquid impermeable backsheet 2 may include a plastic film, a nonwoven material coated with a liquid impervious material or a hydrophobic nonwoven material which resists liquid penetration.

The topsheet 3 and the backsheet material 2 have a somewhat greater extension in the plane than the absorbent body 4 and extend outside the edges thereof. The layers 2 and 3 are connected to each other within the projecting portions thereof, e.g., by gluing or welding by heat or ultrasonic.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well-known to the person skilled in the art and does therefore not have to be described in detail. The thin absorbent bodies which are common in for example baby diapers and incontinence guards often comprise a compressed mixed or layered structure of cellulosic fluff pulp and superabsorbent.

The diaper/incontinence guard is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of adhesive tape portions 8 or other type of fastening means such as hooks and loop type fasteners.

A pair of belt portions 9 are with one end attached, e.g., glued or ultrasonically welded, to the rear portion 6 of the diaper. The belt portions 9 are with their opposite ends intended to be fastened together, e.g., by means of tape tab 10 which is taped against the outside of the opposite belt portion. Instead of tape tabs there may be another optional fastening means such as hook-and-loop type fasteners. The tape tabs 8 of the front portion 5 or corresponding fastening means are intended to be attached against the outside portions of the belt portions 9 in order to fasten together the diaper/incontinence guard to the desired pantlike shape.

According to an alternative embodiment the belt portions are attached to the front portion 5 of the diaper and thus are intended to be fastened together on the back of the wearer. The fastening means 8 are then arranged on the rear portion 6 of the diaper.

The width of the belt portions 9 should be between 5–20 cm, preferably between 7–15 cm.

The belt portions 9 are preferably a laminate of a carrier material, which forms the outside of the belt, and a soft nonwoven, which forms the inside of the belt intended to be in direct contact with the skin of the user. A suitable nonwoven material can be a spunbond material of, e.g., polypropylene- or polyethylene fibers. Conjugate fibers may also be used. Another suitable nonwoven material can be a carded thermobonded material of, e.g., polypropylene-, polyester- or conjugate fibers. As carrier material a plastic film or another suitable material e.g., nonwoven can be used. The carrier material should be adapted to function as a reception surface for the fastening means 8 and 10, wherein in the case where these fastening means comprise tape tabs a plastic film is suitable. In the case where other types of fastening means are used instead of tape tabs, e.g., hook and loop fasteners, another type of carrier material is used, which also may function as a reception surface for the present fastening means. Also elastic laminates are suitable to use as material in the belt portions 9.

Figure 2A:
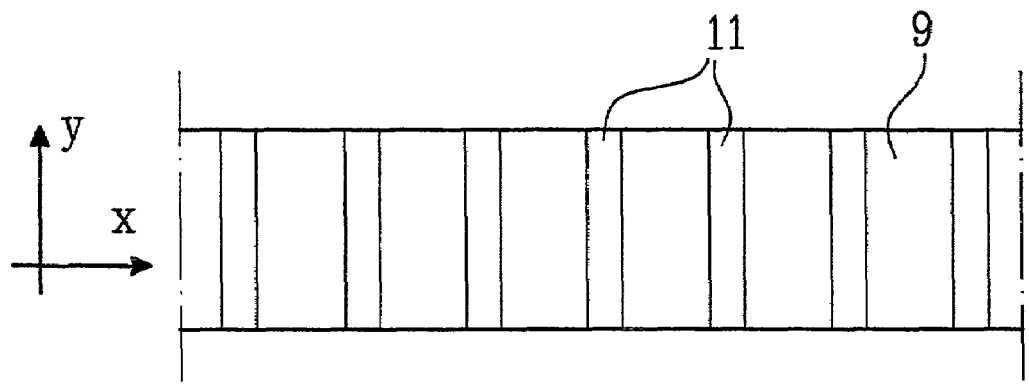
FIG. 2 shows examples of belts to the diaper in FIG. 1.
Figure 2B:
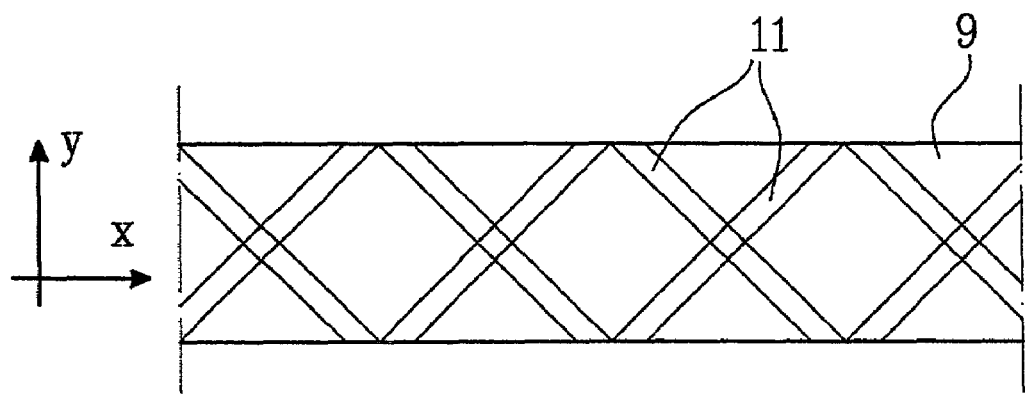

The belt portions 9 are reinforced with stiffening elements 11. These may be arranged across the belt having suitably adapted distances between said stiffening elements 11. The wording "across" used here, means that they extend between the opposite longitudinal edges of the belt portions 9, either essentially perpendicular to these edges or obliquely in relation to these. However, they do not have to extend all the way to the longitudinal edges of the belt portions 9, but may stop slightly inside these edges. It is however preferred that they extend to said longitudinal edges. The stiffening elements 11 may also form a pattern such as a striped pattern (FIG. 2a) or crosswise arranged pattern (FIG. 2b) or other suitable pattern being repeated in the longitudinal direction x of the belt. In the case where the stiffening elements are arranged in a striped pattern, the stripes may among each other have different widths in x direction, (x direction means here longitudinally to the belt). The stiffening element 11 preferably include the same material already being in the belt portions 9 or in the rest of the diaper. Since the product is a disposable article, the material used should be intended for this purpose and not be to costly. The stiffening elements 11 may for instance include different kinds of nonwoven material or plastic material and be obtained by adhesive joining, welding or melting of materials. A kind of a so-called hotmelt adhesive may also be used to obtain the stiffening elements 11. The stiffening elements 11 keep the belt extended in y direction (the expression y direction means here the width of the belt) in order to avoid that the belt sags, when it is being applied around the waist of the wearer. This makes the belt more comfortable to wear for the user.

The invention is of course not limited to the above described embodiment but can be modified within the scope of the claims.

What is claimed is:

1. Absorbent article comprising:
   a liquid permeable topsheet, a liquid impermeable backsheet and an absorbent body enclosed therebetween, said article having a front portion, a rear portion and a crotch portion therebetween, and
   a pair of belt portions attached to one of the rear portion and the front portion of the article, and fastening means provided on the other of the front portion and the rear portion, said belt portions first being attached to each other around the waist of a wearer when donning said absorbent article and said fastening means then being attached to an outer surface of the belt portions such that the article will assume a pantlike shape having a waist portion,
   wherein the belt portions are permanently integrated with one of the rear portion and the front portion of the article and thereby form a part of the waist portion of the article,
   wherein each of the belt portions includes a plurality of stiffening elements discontinuously arranged in the longitudinal direction of the belt portions so as to prevent sagging of the belt portions, the largest extension of the stiffening elements being arranged substantially across the longitudinal direction of the belt portions, and
   wherein aid plurality of stiffening elements maintain the belt portions extended in a direction perpendicular to the longitudinal direction in order to avoid sagging of the belt portions when applied around the waist of the wearer.

2. Absorbent article according to claim 1, wherein the stiffening elements are arranged in a pattern, repeated along the longitudinal direction of the belt portions.

3. Absorbent article according to claim 2, wherein the stiffening elements are arranged in a striped pattern.

4. Absorbent article according to claim 2, wherein the stiffening elements are arranged in a crosswise pattern.

5. Absorbent article according to claim 1, wherein the article comprises a diaper.

6. Absorbent article according to claim 1, wherein the article comprises an incontinence guard.

* * * * *